United States Patent [19]
Wilkes et al.

[11] Patent Number: 5,551,781
[45] Date of Patent: Sep. 3, 1996

[54] STERILIZABLE CONTAINER AND METHOD OF FABRICATION

[76] Inventors: Kenneth R. Wilkes, 55 Brookwood Rd., Asheville, N.C. 28804; Chatchai Taosuwan, 2330 Agostino Dr., Rowland Heights, Calif. 91748; David M. Factor, 15251 Alondra Blvd., La Mirada, Calif. 90638

[21] Appl. No.: 426,103

[22] Filed: Apr. 21, 1995

[51] Int. Cl.$^6$ ................................................ B65D 33/00
[52] U.S. Cl. ......................... 383/205; 383/200; 206/439
[58] Field of Search ........................... 206/439; 383/200, 383/205, 210, 211, 66; 493/212, 223, 225, 923, 930

[56] References Cited

U.S. PATENT DOCUMENTS

| | | | |
|---|---|---|---|
| 2,991,000 | 7/1961 | Spees | 383/205 |
| 3,140,815 | 7/1964 | Majesky | 383/205 |
| 3,472,369 | 10/1969 | Schuster | 206/63.2 |
| 3,685,720 | 8/1972 | Brady | 229/62 |
| 3,754,700 | 8/1973 | Bonk | 229/62 |
| 3,761,013 | 9/1973 | Schuster | 229/62 |
| 4,057,144 | 11/1977 | Schuster | 206/439 |
| 4,367,816 | 1/1983 | Wilkes | 206/439 |
| 4,550,831 | 11/1985 | Whitford | 206/439 |

*Primary Examiner*—David T. Fidei
*Attorney, Agent, or Firm*—Saul Epstein

[57] ABSTRACT

A sterilizable package having at least one flexible plastic wall, and having an access opening therein covered by a peelable two layered tear strip, including a porous membrane and a plastic interlayer, which interlayer has an opening substantially matching the access opening, where the opening in the plastic interlayer is 25% or more of the width of the interlayer. The interlayer is kept from deforming during fabrication of the pouch by tack sealing it to the flexible wall of the package, and cutting the access opening and the opening in the interlayer simultaneously after the interlayer is tack sealed to the front sheet.

6 Claims, 2 Drawing Sheets

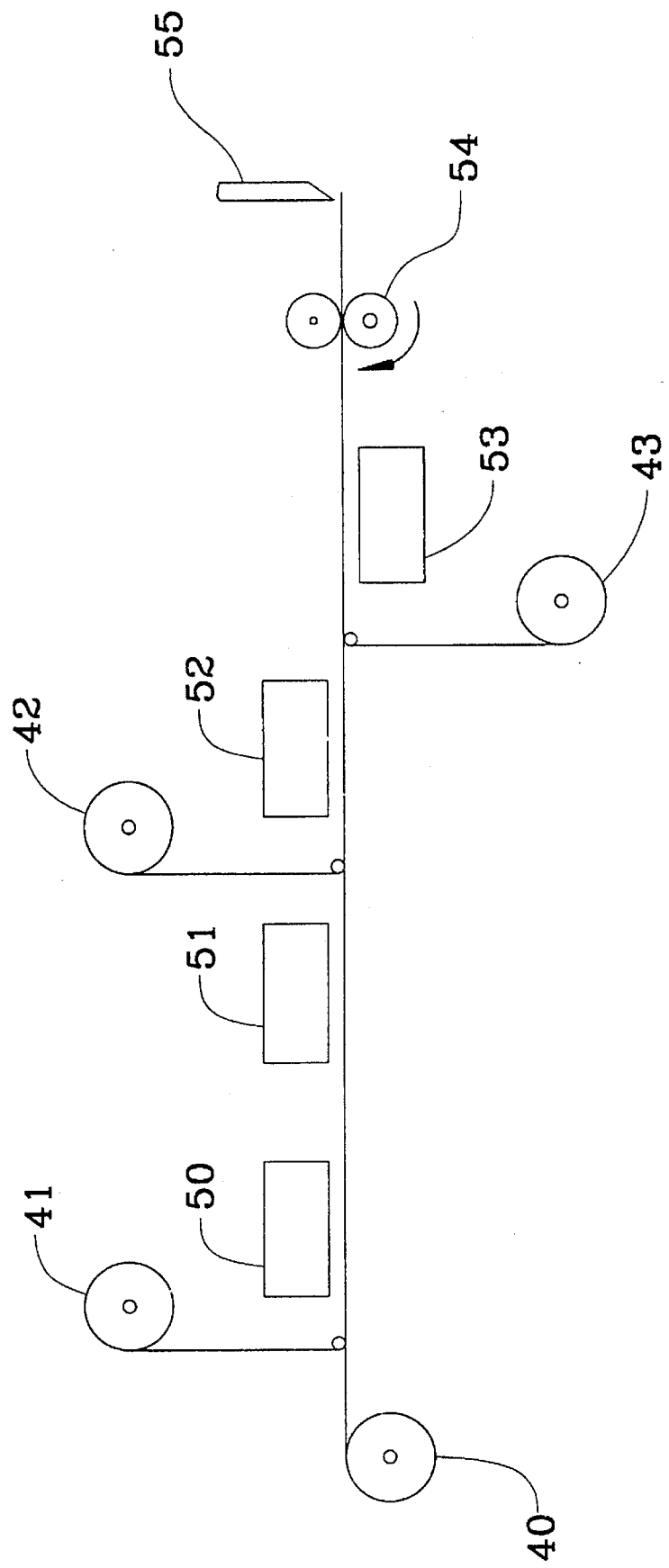

STERILIZABLE CONTAINER AND METHOD OF FABRICATION

FIELD OF THE INVENTION

This invention relates to containers intended for storing items, such as for example medical or surgical instruments, in a sterile condition. Such containers may take the form of pouches or they may involve other package configurations.

BACKGROUND OF THE INVENTION

One popular form of sterilizable container often used to store medical or surgical instruments is a pouch comprised of two sheets of plastic, for example low density polyethylene, positioned face to face and sealed around their common periphery with heat seals. An access opening is cut in one of the sheets, and the opening covered with a porous membrane sealed to the pouch around the opening. The porous membrane in this construction serves two functions; it covers the access opening, and it provides a means to sterilize the contents of the pouch. The membrane is sealed to the pouch with peelable seals so that it can be easily peeled from the pouch, and the contents removed through the access opening. Also, the membrane is made porous in order that the contents of the pouch can be sterilized using a sterilizing gas (chemical or steam) after the pouch has been sealed. The porosity of the membrane is such that the sterilizing gas can pass through it, yet the membrane forms a sterile barrier against bacteria or the like. Porous membranes for such pouches (called "tear strips") are commonly made of surgical grade paper or spunbonded olefin, which is sold by the Du Pont Company under the trademark Tyvek.

The "breathability" of tear strips is an important issue in the construction of sterilizable pouches. Is is desirable that the tear strip offer as little resistance as possible to the flow of the sterilizing gas in order that the sterilization cycle be as short as possible. Unfortunately, in order to form a peelable seal with low density polyethylene, paper or Tyvek must be coated or otherwise treated, and the required treatment is such that the membrane's porosity is substantially reduced. The sterilization cycle using such tear strip materials is usually substantially longer than desired. Consequently, it is preferred that uncoated tear strips be used.

This problem was addressed by the present inventor in U.S. Pat. No. 4,367,816. The solution there presented was to use a two layered tear strip, with the top layer being an uncoated porous membrane, and the second being an interlayer between the porous membrane and the pouch proper. The interlayer is a sheet (generally plastic) which can form a peelable seal to the material of the pouch, and also seal to the uncoated membrane. The interlayer disclosed in the '816 patent was provided with small holes, perforations, or a slit to allow the sterilizing gas to pass.

While the prior invention was generally a great improvement over the prior art, a problem can possibly arise in using the construction disclosed therein, particularly with larger pouches. When the sterilzing gas is flowing outward, the interlayer sheet tends to press against the porous membrane, and in some cases this could result in reducing the area of the membrane through which the gas is flowing, and thereby impede gas flow.

Using existing manufacturing techniques, it has not been practical to cut large openings in the interlayer. If the open area of the interlayer is made large, i.e., if the width of the opening is made more than about 25% of the width of the sheet, certain manufacturing difficulties arise, as will be discussed further below. These difficulties are overcome by the method of manufacturing disclosed in this specification, and using the method disclosed, it becomes practical to fabricate pouches wherein the breathing area for outgoing gases is substantially the same as for incoming gases. The terms "length" and "width" used in this document refer to the direction that the webs in the pouch making machine move during fabrication, and crosswise to the machine direction, respectively. Using this convention, the resulting pouches may very well (in fact are likely to) have "widths" which are greater than their "lengths".

SUMMARY OF THE INVENTION

A presently preferred embodiment of a pouch embodying the present invention is comprised of a rear sheet and a front sheet placed face to face and seamed around their common periphery. Both sheets are preferably low density polyethylene. For clarity of explanation, it will be convenient to describe the invented pouch in connection with a specific pouch, but it will be understood that the dimensions cited are merely illustrative, and are not intended to be limiting. The exemplary pouch described herein may be 20 inches long by 24 inches wide. A 3 inch wide by 17 inch long access opening is centered along the length of the pouch about 7 inches from one edge. It is desirable to have a relatively large access opening for ease in removing the stored product. Covering the access opening is a coated high density polyethylene sheet (the interlayer) about 7 inches wide and the same length as the pouch. And covering the interlayer is a paper or spunbonded olefin porous membrane having substantially the same size as the interlayer. The paper or spunbonded olefin sheet, being porous, allows the passage of sterilizing gas, but it is not so porous as to allow the passage of bacteria or the like. The larger the area of the porus membrane, the shorter will be the sterilization cycle, hence large area porous membranes are desirable. The interlayer is coated on each side (preferably by coextrusion) with thin layers of materials which have the desired bonding characteristics to the pouch material and to the porous membrane respectively. It is preferred that the interlayer form a tight bond to the porous membrane, but be peelable from the low density polyethylene. Various blends of ethyl vinyl acetate (EVA) and low density polyethylene are commonly used for this purpose, as is known to those skilled in the art. The interlayer has an opening which matches the access opening in the front low density polyethylene sheet, hence the breathing area of the porous membrane is not covered by the interlayer, and it cannot impede sterilizing gas flow. For the reason which will be discussed further below, the pouch as described above cannot be successfully fabricated using prior art techniques.

Pouches are generally manufactured on a machine in which the materials which make up the various layers of the pouch are supplied as continous webs from large rolls of the respective materials. As the webs pass through the machine, required openings are cut, and the webs are sealed to each other to form the pouch. Finally, the finished pouches are cut from the webs. Four webs are required to fabricate the pouch described in this specification, two low density polyethylene webs for the rear and front sheets, a relatively narrow high density polyetylene web to form the interlayer, and a porous membrane web, the same width as the interlayer. The two low density polyethylene webs and the porous membrane web do not create particular problems in manufacturing, but the interlayer web will be found to cause extreme fabrication difficulties absent the method of this invention. The reason for the difficulties is that the interlayer of the present invention has a relatively large cut out area. If more than about 25% of the width of a plastic web is cut out, tension in the web tends to cause the sides of the web to bow in, and wrinkles to appear in the web. This problem is avoided in the invented fabrication method by tack sealing the relatively narrow interlayer to the front sheet before the access opening is cut. The tendency of the narrow interlayer web to collapse and wrinkle is avoided by the support of the front sheet. An opening is then cut in the front sheet and the interlayer at the same time, after the tack seals are made fastening the two webs together. The opening cut in the front sheet eventually becomes the access opening. After this opening is cut, the porous membrane, the interlayer, and the front sheet are seamed to each other by line seals, and then the front and rear sheets are similarly seamed to complete fabrication of the invented container.

A more complete understanding of the invention can be had by reference to the following detailed description and the attached drawings.

BRIEF DESCRIPTION OF THE DRAWINGS

FIG. 2 is a diagrammatic side view of a machine for making the invented pouch according to the invented method.

DETAILED DESCRIPTION OF THE INVENTION

Figure 1:
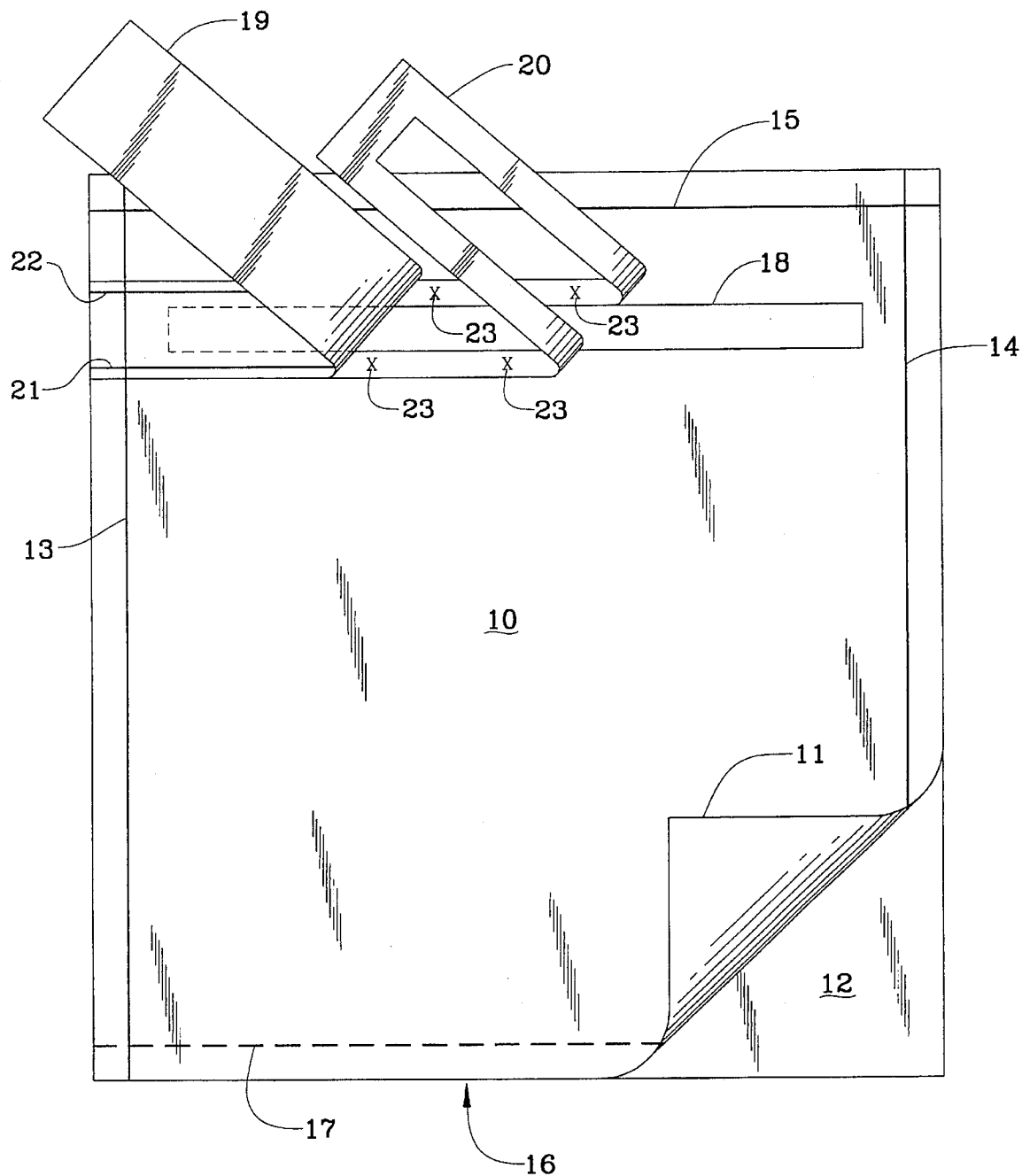
FIG. 1 is a plan view of a pouch made according to the present invention. Portions of the pouch are peeled away from their normal positions in order to illustrate the construction.

FIG. 1 shows a plan view of a pouch embodying the present invention, with some of the elements partially peeled away to show the construction. As seen in FIG. 1, the front sheet 10 has a corner 11 turned up so that the rear sheet 12 can be seen. In an actual pouch, of course, there would be no turned up corner 11. The front and rear sheets 10 and 12, which make up the container portion of the pouch, are preferably made of flexible low density polyethylene, and are seamed together by heat sealing along lines 13, 14, and 15. The pouch is left open along side 16 at the time of manufacture, but is heat sealed in a similar fashion after the item to be stored in the pouch is inserted. A seam 17 along side 16 is shown dotted to indicate that this seam is made at a later time. The access opening 18, cut in front sheet 10, is covered by a tear strip comprised of porous membrane 19 and interlayer 20. The tear strip is attached to the front sheet 10 by heat seals 13, 14, 21, and 22. The porous membrane is preferably made of surgical paper or Tyvek, and the interlayer of high density polyethylene. The interlayer is coated on both sides in order to achieve the desired bonding to the front sheet and to the porous membrane. The bond between the interlayer and the front sheet should be a "peelable" bond, i.e., one that is strong, yet permitting the interlayer to be peeled from the front sheet, but the bond to the porous membrane preferably will tear the membrane before the bond separates. Various substances can be coextruded onto the surfaces of the interlayer to achieve the desired bonds; commonly various blends of ethyl vinyl acetate (EVA) and low density polyethylene are used for this purpose.

FIG. 2 is a diagrammatic side view of a machine for fabricating the pouch described above. The design of pouch making machines is well known in the art, and it is not deemed necessary to provide specific details of construction. As seen in FIG. 2, the web which forms the front sheet is supplied from roll 40, and the interlayer from roll 41. In order to avoid the problem noted in the Summary of the Invention section, i.e., that a web which contains a cutout portion greater than about 25% of its width (the direction normal to the motion of the web) will deform under the tensile forces needed to move the web along its path, the interlayer web is tack sealed to the front sheet at station 50 (before the opening is cut in the interlayer). Tack seals 23 can be seen in FIG. 1. A sufficient number of tack seals 23 are used to provide the needed stabilization. By attaching the interlayer to the front sheet before making any cuts, the interlayer is stabilized, and will not deform. At station 51, the access opening 18 is cut through both the front sheet 10 and the interlayer 20.

The porous membrane web is supplied from roll 42 between stations 51 and 52 of the pouch making machine, and the seams 21 and 22 are formed at station 52, as are the small sections of seams 13 and 14 between seams 21 and 22. These seams bond the porous membrane to the interlayer and the interlayer to the front sheet, covering the access opening 18.

The rear sheet is supplied from roll 43, and seams 13, 14, and 15 are formed at station 53. Rollers 54 provide the motive power to pull the webs through the machine, and knife 55 cuts the completed pouches off the composite web.

What has been described is a novel sterilizable package for storing items in a sterile condition, and a method for making the package. A presently preferred embodiment of the invention has been described, but it will be evident to those skilled in the art that many variations and adaptations of the principles disclosed may be made without departing from the spirit of the invention. By way of example, the rear sheet 12, disclosed as a flexible plastic sheet, could be replaced by a rigid dish to make a different embodiment of the invention. The foregoing is but one example of the variants which are envisioned as being within the spirit of the invention. Many others will no doubt occur to those skilled in the art.

We claim:

1. A sterilizable package for storing sterile items which comprises:
    a sealed container having at least one flexible plastic wall, said flexible wall of said container having an access opening therein with a predetermined length and width; and
    a tear strip peelably sealed over said access opening, said tear strip comprising:
    a porous membrane,
    an interlayer between said porous membrane and said sealed container and sealed to both, said interlayer having an opening therein substantially the same size as said access opening, the width of said opening in said interlayer being 25% or more of the width of said interlayer.

2. A sterilizable package as recited in claim 1 wherein said porous membrane is fabricated from uncoated surgical paper.

3. A sterilizable package as recited in claim 1 wherein said porous membrane is fabricated from uncoated spunbonded olefin.

4. A sterilizable package as recited in claim 1 wherein said container is comprised of two substantially rectangular sheets of flexible plastic sealed together around their edges.

5. A method for fabricating and attaching a tear strip to a wall of a sterilizable package which comprises the steps of:

providing a first web of flexible plastic having a first width, said first web being intended to form a wall of said sterilizable package;

providing a second web of flexible plastic having a second width smaller than said first width, the faces of said first and second webs being in contact;

tack sealing said second web to said first web with a plurality of tack seals adjacent the edges of said second web;

cutting an access opening through said first and second webs after said second web has been tack sealed to said first web;

providing a third web of porous material, said third web being in contact with said second web; and sealing said first, second, and third webs together around the periphery of said access opening.

6. The method as recited in claim 5 wherein the joint between said first and second webs is a peelable seal.

* * * * *